United States Patent
Xiao et al.

(10) Patent No.: US 7,371,875 B2
(45) Date of Patent: May 13, 2008

(54) CYTOTOXIC AGENTS AND METHODS OF USE

(75) Inventors: Xiao-Yi Xiao, San Diego, CA (US); Dinesh V. Patel, Fremont, CA (US)

(73) Assignee: Miikana Therapeutics, Inc., Rockville, MD (US)

( * ) Notice: Subject to any disclaimer, the term of this patent is extended or adjusted under 35 U.S.C. 154(b) by 29 days.

(21) Appl. No.: 11/077,887

(22) Filed: Mar. 11, 2005

(65) Prior Publication Data

US 2005/0203162 A1 Sep. 15, 2005

Related U.S. Application Data

(60) Provisional application No. 60/552,511, filed on Mar. 12, 2004.

(51) Int. Cl.
*A01N 43/02* (2006.01)
*C07D 493/00* (2006.01)
*C07D 498/00* (2006.01)

(52) U.S. Cl. ............... 549/510; 549/200; 548/125; 548/126; 548/400; 548/452; 514/449

(58) Field of Classification Search ......... 549/200, 549/510; 548/125, 126, 400, 452; 514/449
See application file for complete search history.

(56) References Cited

U.S. PATENT DOCUMENTS 5,011,472 A   4/1991 Aebischer et al.
5,023,252 A   6/1991 Hseih

FOREIGN PATENT DOCUMENTS

| WO | WO 96/32105 |   | 10/1996 |
|----|-------------|---|---------|
| WO | WO 96/32105 | * | 12/1996 |
| WO | WO 91/16322 |   | 10/2001 |
| WO | WO 02/47610 | * | 6/2002  |

OTHER PUBLICATIONS

Seemuller, et al. "Proteasome from Thermoplasma acidophilum: A Threonine Protease" *Science* 268:579-582 (1995).
Fenteany, et al. "Inhibition of Proteasome Activities and Subunit-Specific Amino-Terminal Threonine Modification by Lactacystin" *Science* 268:726-731 (1995).
Shah et al. "Early clinical experience with the novel proteasome inhibitor PS-519" *Br. J. Clin. Charmacol* 54:269-276 (2002).
Goldberg et al. "Not just research tools-proteasome inhibitors offer therapeutic promise" *Nature Medicine* 8:338-340 (2002).
Kolb et al. "Catalytic Asymmetric Dihydroxylation" *Chem. Rev.* 94:2483-2547 (1994).
Pink, et al. "PS-341 enhances chemotherapeutic effect in human xenograft models" *Proc. Am. Assoc. Cancer Res.* 43:158 (2002).

* cited by examiner

*Primary Examiner*—Bruck Kifle
*Assistant Examiner*—Paul V. Ward
(74) *Attorney, Agent, or Firm*—King & Spalding

(57) ABSTRACT

Disclosed are compounds that inhibit proteasomic activity in cells. Also disclosed are pharmaceutical compositions comprising such compounds as well as methods to treat conditions, particularly cell proliferative conditions, such as cancer and inflammatory conditions.

17 Claims, No Drawings

CYTOTOXIC AGENTS AND METHODS OF USE

CROSS-REFERENCE TO RELATED APPLICATIONS

This application claims the benefit under 35 U.S.C. §119 (e) of U.S. Provisional Patent Application Ser. No. 60/552,511 filed Mar. 12, 2004 which application is incorporated herein by reference in its entirety.

BACKGROUND OF THE INVENTION

1. Field of the Invention

This invention relates to proteasome inhibitory compounds. This invention is also directed to pharmaceutical compositions comprising such compounds as well as to treat conditions, particularly cancer and inflammation, in which inhibition of proteasomic activity provides therapeutic benefit.

REFERENCES

The following publications are cited in this application as superscript numbers:

[1] Seemuller, et al., "Proteasome from *Thermoplasma acidophilum*—a threonine protease", 1995 Science; 268: 579-582
[2] Fenteany, et al. "Inhibition of proteasome activities and subunit-specific amino-terminal threonine modification by lactacystin" 1995 Science; 268:726-731
[3] Goldberg A L, Rock K "Not just research tools—proteasome inhibitors offer therapeutic promises" 2002 Nature Med; 8 (4): 338-340
[4] Shah, et al., "Early clinical experience with the novel proteasome inhibitor PS-519" 2002 Br J Clin Pharmacol; 54: 269-276

All of the above publications are herein incorporated by reference in their entireties to the same extent as if each individual publication was specifically and individually indicated to be incorporated by reference in its entirety.

2. State of the Art

The ubiquitin-proteasome pathway is the major proteolytic machinery in the nucleus and cytosol of the eukaryotic cells. This pathway is responsible for the selective degradation of a large variety of cellular proteins and is essential for many regulatory cellular processes, such as the regulation of tumor suppressor p53, and the transcription factor, nuclear factor κB (NF-κB), which play key roles in pathogenesis of many cancer, inflammatory and neoplastic diseases.

The 26S proteasome is a large (2.5 MDa), ATP-dependent, multi-functional complex of proteolytic enzymes and ancillary proteins. It consists of a core proteolytic particle, the 20S proteasome, sandwiched between two regulatory "caps" (the 19S complexes). Its six proteolytic active sites are segregated in compartments within the hollow, cylindrically shaped 20S proteasome, which consists of four stacked rings (two outer α-rings and two inner β-rings). Each β-ring has three proteolytic active sites with different specificities, one "chymotrypsin-like" site preferring hydrophobic residues, one "trypsin-like" active site for basic amino acids, and one "caspase-like" site with specificity for acidic residues.

The proteasome belongs to a recently described class of proteolytic enzymes called threonine proteases, since it uses the N-terminal threonines of its β-subunits as the nucleophiles in the proteolytic processes.[1] X-ray diffraction studies with inhibitor-protein complexes strongly indicate that the hydroxyl group, instead of the amino group, of the threonine is the attacking nucleophile in the cleavage of peptide bonds. Evidence from studies of different classes of proteasome inhibitors as well as X-ray diffraction suggest a catalytic mechanism closely resembling that of serine and cysteine proteases, with the exception that the proteasome uses the N-terminal amino group of the threonine, instead of a classic catalytic triad, to accept the proton from the attacking hydroxyl group and facilitate peptide bond cleavage.[2]

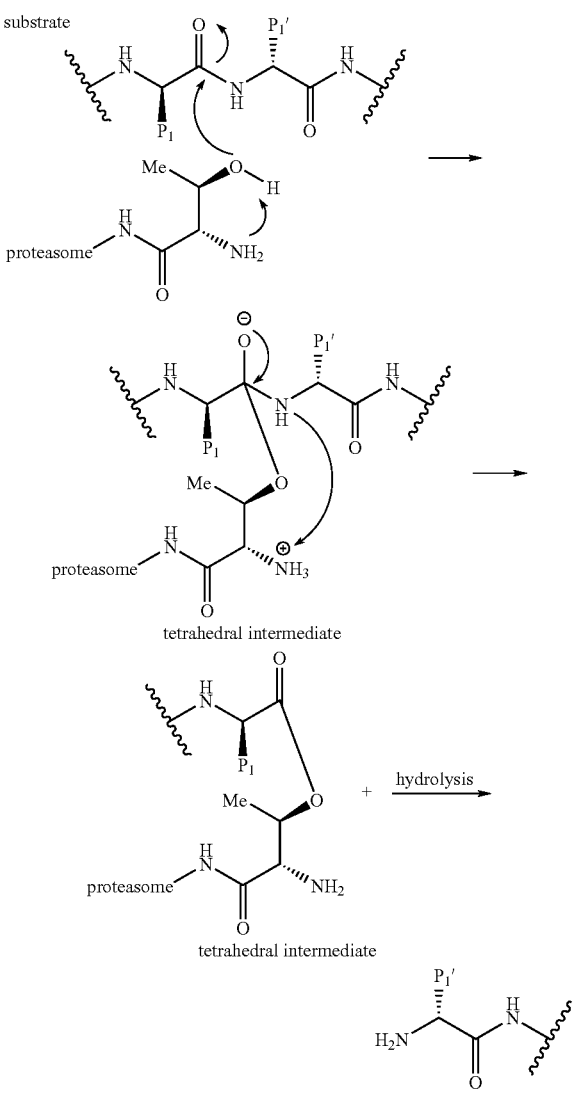

Chemotherapy is the first line of treatment for a number of neoplastic diseases (cancers). Over the past thirty years, the arsenal of chemotherapeutic agents has expanded from early drugs targeted at interfering with DNA synthesis and replication to newer immunotherapeutic agents that target specific cell types or cell processes; however, chemotherapeutics that target cell proliferative processes, including cytotoxic agents, remain a mainstay of cancer chemotherapy.

Cytotoxic agents are compounds that kill cells, particularly highly proliferative cells. These compounds have found widespread use in the treatment of cancer, as well as various types of inflammatory conditions. In general, such agents, due their very nature as cytotoxic agents, are toxic to normal, as well as to diseased cells.

Certain forms of inflammation are also amenable to cytotoxic therapy. For example, cytotoxic agents have become important components of immunosuppressive regimens for rheumatoid arthritis. More recently, it has become apparent that inflammation and immunologic response also contribute to neurodegeneration in people with Alzheimer's Disease. Excessive glial activation and proliferation are thought to be pivotal events that hasten the demise of synapses and neurons in this disorder. Cytotoxic agents are also used in as adjunct therapy in organ transplantation, and as treatments for sickle cell anemia and psoriasis.

In view of the above, there is an ongoing need for cytotoxic agents with higher therapeutic indices. More specifically, proteosome inhibitors represent a new class of mechanism-based cytotoxic agents,[3] which recently have shown effectiveness in the treatment of cancer, inflammatory, and ischemic disorders as exemplified by the recently approved multiple myeloma drug bortezomib (VELCADE™; PS-341) and the late stage clinic trial compound PS-519 for stroke.[4] However, currently available proteasome inhibitors suffer from one or more of the following drawbacks to effective therapeutics: (i) they are either synthetic peptides, such as bortezomib, which has a low therapeutic index and limited oral bioavailability; (ii) they are complex natural products, which are not readily or cost-effectively translatable into cost-effective drugs; (iii) they may contain unstable chemical functionalities such as β-lactones, aldehydes, or boronic acids; (iv) they are alkylating agents such as Michael acceptors (e.g., vinyl sulfones), which are highly toxic to the organism.

The present invention provides proteosome inhibitory compounds that overcome one or more of the limitations mentioned above, and which exhibit more desirable stability, toxicity and/or oral bioavailability than are seen in currently available proteosome inhibitors.

SUMMARY OF THE INVENTION

This invention provides compounds which exhibit proteasome inhibition activity and, accordingly, are useful as anti-proliferative agents in the treatment of proliferative disorders, such as cancer and inflammation.

Accordingly, in one of its composition aspects, this invention is directed to a compound of formula I:

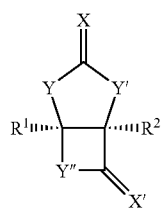

I wherein:
   $R^1$ is selected from the group consisting of alkyl, substituted alkyl cycloalkyl, substituted cycloalkyl, cycloalkenyl, substituted cycloalkenyl, alkenyl, substituted alkenyl, alkynyl, substituted alkynyl, aryl and substituted aryl;

$R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;

X and X' are independently selected from the group consisting of oxygen, sulfur and $NR^3$ where $R^3$ is selected from the group consisting of hydrogen, hydroxyl, amino, alkyl, substituted alkyl, cycloalkyl, substituted cycloalkyl, aryl, substituted aryl, alkoxy, aryloxy, alkylamino, arylamino, and acylamino;

Y, Y' and Y" are independently selected from the group consisting of —O—, —N($R^3$)—, —S— and —C($R^4$)($R^5$)— where $R^3$ is as defined above and $R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, substituted aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further $R^4$ and $R^5$ together with the carbon atom pendent thereto form an optionally substituted vinyl group; or prodrugs, isomers and pharmaceutically acceptable salts thereof.

In another of its composition aspects, this invention is directed to a compound of formula II:

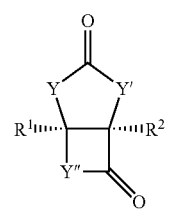

II wherein:
   $R^1$ is selected from the group consisting of alkyl, substituted alkyl, cycloalkyl, substituted cycloalkyl, cycloalkenyl, substituted cycloalkenyl, alkenyl, substituted alkenyl, alkynyl, substituted alkynyl, aryl and substituted aryl;

$R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;

Y, Y' and Y" are independently selected from the group consisting of —O—, —N($R^3$)—, —S— and —C($R^4$)($R^5$)— where $R^3$ is selected from the group consisting of hydrogen, hydroxyl, amino, alkyl, substituted alkyl, cycloalkyl, substituted cycloalkyl, aryl, substituted aryl, alkoxy, aryloxy, alkylamino, arylamino, and acylamino; and $R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, substituted aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further R⁴ and R⁵ together with the carbon atom pendent thereto form an optionally substituted vinyl group; or prodrugs, isomers and pharmaceutically acceptable salts thereof.

In another of its composition aspects, this invention is directed to a compound of formula III:

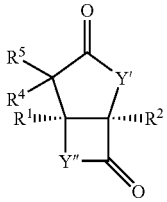

III wherein:

- $R^1$ is selected from the group consisting of alkyl, substituted alkyl, cycloalkyl, substituted cycloalkyl, cycloalkenyl, substituted cycloalkenyl, alkenyl, substituted alkenyl, alkynyl, substituted alkynyl, aryl and substituted aryl;
- $R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;
- $R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, substituted aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further $R^4$ and $R^5$ together with the carbon atom pendent thereto form an optionally substituted vinyl group;
- Y' and Y" are independently selected from the group consisting of —O—, —N(R³)—, —S— and —C(R⁴)(R⁵)— where R³ is selected from the group consisting of hydrogen, hydroxyl, amino, alkyl, substituted alkyl, cycloalkyl, substituted cycloalkyl, aryl, substituted aryl, alkoxy, aryloxy, alkylamino, arylamino, and acylamino; or prodrugs, isomers and pharmaceutically acceptable salts thereof.

In another of its composition aspects, this invention is directed to a compound of formula IV:

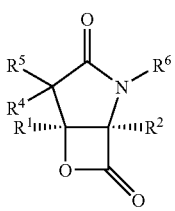

IV wherein:

- $R^1$ is selected from the group consisting of alkyl, substituted alkyl, cycloalkyl, substituted cycloalkyl, cycloalkenyl, substituted cycloalkenyl, alkenyl, substituted alkenyl, alkynyl, substituted alkynyl, aryl and substituted aryl;
- $R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;
- $R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, substituted aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further $R^4$ and $R^5$ together with the carbon atom pendent thereto form an optionally substituted vinyl group;
- $R^6$ is selected from the group consisting of hydrogen, hydroxyl, amino, substituted amino, acylamino, alkyl, substituted alkyl, cycloalkyl, substituted cycloalkyl, aryl, substituted aryl, alkoxy, substituted alkoxy, aryloxy, and substituted aryloxy, or prodrugs, isomers and pharmaceutically acceptable salts thereof.

In another of its composition aspects, this invention is directed to a compound of formula V:

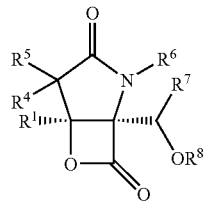

V wherein:

- $R^1$ is selected from the group consisting of alkyl, substituted alkyl, cycloalkyl, substituted cycloalkyl, cycloalkenyl, substituted cycloalkenyl, alkenyl, substituted alkenyl, alkynyl, substituted alkynyl, aryl and substituted aryl;
- $R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;
- $R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, substituted aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further $R^4$ and $R^5$ together with the carbon atom pendent thereto form an optionally substituted vinyl group;
- $R^6$ is selected from the group consisting of hydrogen, hydroxyl, amino, substituted amino, acylamino, alkyl, substituted alkyl, cycloalkyl, substituted cycloalkyl, aryl, substituted aryl, alkoxy, substituted alkoxy, aryloxy, and substituted aryloxy;

R$^7$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;

R$^8$ is selected from the group consisting of hydrogen, alkyl, substituted alkyl, cycloalkyl, substituted cycloalkyl, aryl and substituted aryl; or prodrugs, isomers and pharmaceutically acceptable salts thereof.

Preferably, R$^1$ is methyl, trifluoromethyl, methoxymethyl, ethyl, 2-methoxyethyl, n-propyl, iso-propyl, iso-butyl, n-butyl, cyclopropyl, cyclobutyl, cyclopentyl, cyclohexyl, cyclohexenyl, vinyl, ethynyl, allyl, benzyl, phenyl, and the like.

Preferably, R$^2$ is 1-hydroxyl-2-methylpropane-1-yl, 1-hydroxyl-1-cyclohexylmethane-1-yl, and the like.

When Y" is >NR$^3$, then R$^3$ is preferably hydrogen or methoxy.

When Y is >CR$^4$R$^5$, then R$^4$ is preferably (C$_1$-C$_6$)alkyl such as methyl or n-propyl, halo(C$_1$-C$_6$)alkyl such as 2-chloroethane-1-yl and trifluoromethyl, halo such as fluoro and chloro, (C$_1$-C$_6$)alkoxy such as methoxy, (C$_1$-C$_6$)alkylthio such as CH$_3$S—, phenoxy, (C$_1$-C$_6$)alkylamino such as methylamino, (C$_1$-C$_6$)acylamino such as acetylamino and the like.

R$^5$ is preferably hydrogen, fluoro, chloro or R$^4$ and R$^5$ are joined to form a cycloalkyl group such as cyclopropyl or a vinyl group including substituted vinyl, e.g., 2,2-dimethylethylene-1-yl.

Preferably, R$^7$ is (C$_3$-C$_6$)alkyl, cycloalkyl and cycloalkenyl such as iso-propyl, cyclohexyl, cyclohexene-1-yl, and the like.

Preferably, R$^8$ is hydrogen.

In one of its pharmaceutical composition aspect, this invention is directed to a pharmaceutical composition comprising an effective amount of a compound according to any of formulas I-V and a pharmaceutically inert carrier.

In another of its pharmaceutical aspects, this invention is directed to pharmaceutical compositions comprising an effective amount of a compound according to any of formulas I-V, an effective amount of at least one anti-neoplastic agent, and a pharmaceutically inert carrier.

In one of its method aspects, this invention is directed to a method for inhibiting a proliferative disorder in a mammalian patient which method comprises administering to said patient a pharmaceutical composition comprising a pharmaceutically acceptable carrier and a therapeutically effective amount of a compound of formula I-V or a mixture thereof.

In another of its method aspects, this invention is directed to a method for inhibiting a proliferative disorder in a mammalian patient which method comprises administering to said patient a pharmaceutical composition comprising a pharmaceutically acceptable carrier, an effective amount of at least one anti-neoplastic agent, and a therapeutically effective amount of a compound of formula I-V or a mixture thereof.

In yet another of its method aspects, this invention is directed to a method for inhibiting a proliferative disorder in a mammalian patient which method comprises administering to said patient a pharmaceutical composition comprising a pharmaceutically acceptable carrier and a therapeutically effective amount of a compound of formula I-V or a mixture thereof in combination with at least one anti-neoplastic agent.

For the treatment of the above conditions, the compounds of the invention may be advantageously employed in combination with one or more other medicinal agents, more particularly, with other anti-neoplastic (anti-cancer) agents. Examples of anti-neoplastic agents are: platinum coordination compounds for example cisplatin, carboplatin or oxalyplatin; taxane compounds for example paclitaxel or docetaxel; topoisomerase I inhibitors such as camptothecin compounds for example irinotecan or topotecan; topoisomerase II inhibitors such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents such as nitrogen mustard or nitrosourea for example cyclophosphamide, chlorambucil, carmustine or lomustine; anti-tumour anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; histone deacetylase (HDAC) inhibitors, such as trichostatin A (TSA) or suberoylanilide hydroxamic acid (SAHA); angiogenesis inhibitors, such as bevacizumab; or other proteosome inhibitors, for example bortexomib, PS-519, lactacystin, omuralide, salinosoramide A, or epoxomicin. Compounds of the present invention can also be used in conjunction with other cancer treatment modalities, such as ablative surgery; radiation therapy; phototherapy, with or without the use of a photosensitizing agent, such as porfimer sodium; bone marrow transplantation; stem cell transplantation; hyperthermia; cryosurgery; laser therapy; immunotherapy, such as *Bacillus* Calmette-Guerin (BCT) or levamisol; cancer vaccines.

In still another of its pharmaceutical aspects, this invention is directed to pharmaceutical compositions comprising an effective amount of a compound according to any of formulas I-V, and an effective amount of at least one anti-inflammatory agent, and a pharmaceutically inert carrier.

In one of its method aspects, this invention is directed to a method for inducing cytotoxic activity in a mammalian patient suffering from a condition characterized by cell proliferation, which method comprises administering to said patient a pharmaceutical composition comprising a pharmaceutically acceptable carrier and a therapeutically effective amount of a compound of formula I-V or a mixture thereof.

In another of its method aspects, this invention is directed to a method for inhibiting cellular proteosomic activity in a mammalian patient which method comprises administering to said patient a pharmaceutical composition comprising a pharmaceutically acceptable carrier, an effective amount of at least one anti-cancer agent, and a therapeutically effective amount of a compound of formula I-V or a mixture thereof.

For treatment of inflammatory disorders, the compounds of the invention may be advantageously employed in combination with one or more other medicinal agents, more particularly, with other anti-inflammatory medicaments, such as are described herein and are well known in the art.

Preferred compounds of this invention include compounds 1-15 as identified in Table I below (including pharmaceutical salts thereof as well as positional and stereo isomers and prodrugs thereof).

TABLE I
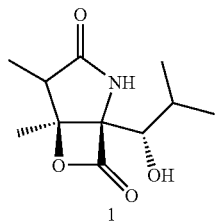
1
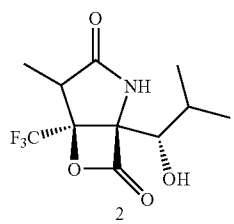
2
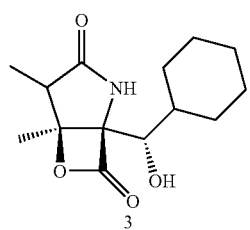
3
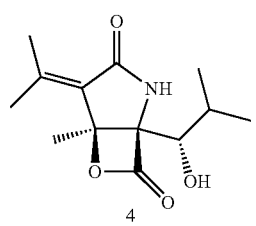
4
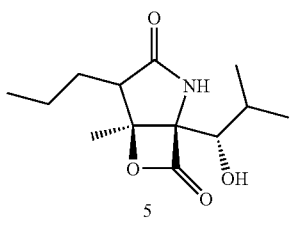
5
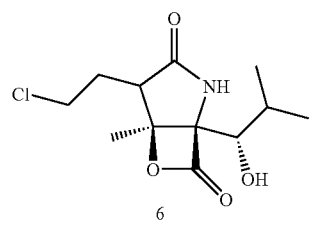
6
TABLE I-continued
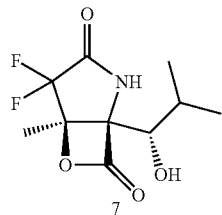
7
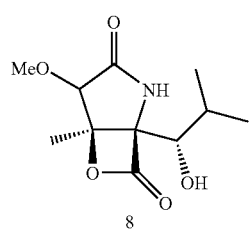
8
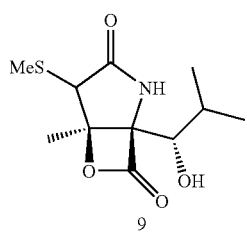
9
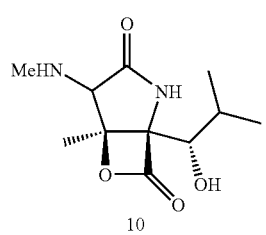
10
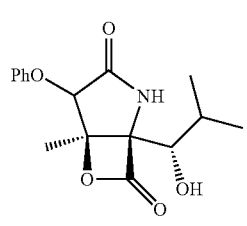
11
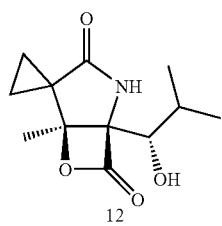
12

TABLE I-continued

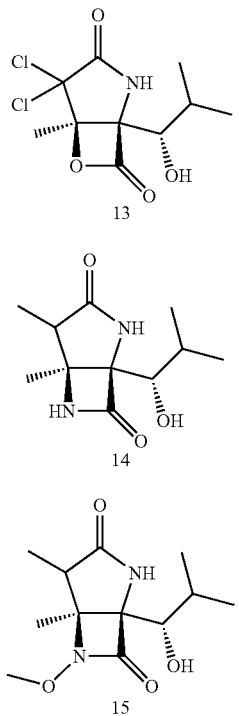

DETAILED DESCRIPTION OF THE INVENTION

As noted above, this invention is directed to compounds, pharmaceutical compositions and methods for inhibiting cellular proteasomic activity, and which have utility in treating proliferative disorders such as cancer, and inflammatory disorders.

This section will provide guidance for practicing the present invention.

Definitions

Unless otherwise limited by a specific recitation herein, the following terms have the following meanings;

"Alkyl" refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to a monovalent alkyl group having from 1 to 3, and preferably 1 to 2, substituents selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Acyloxy" refers to the groups H—C(O)O—, alkyl-C(O)O—, substituted alkyl-C(O)O—, alkenyl-C(O)O—, substituted alkenyl-C(O)O—, cycloalkyl-C(O)O—, substituted cycloalkyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—.

"Acylthio" refers to the groups H—C(O)S—, alkyl-C(O)S—, substituted alkyl-C(O)S—, alkenyl-C(O)S—, substituted alkenyl-C(O)S—, cycloalkyl-C(O)S—, substituted cycloalkyl-C(O)S—, aryl-C(O)S—, substituted aryl-C(O)S—, heteroaryl-C(O)S—, substituted heteroaryl-C(O)S—, heterocyclic-C(O)S—, and substituted heterocyclic-C(O)S—.

"Alkylthio" refers to the group "alkyl-S-" which includes, by way of example, methylthio, ethylthio, n-propylthio, iso-propylthio, n-butylthio, t-butylthio, sec-butylthio, n-pentylthio and the like.

"Aminoacyl" refers to the group —C(O)NR$^{10}$R$^{10}$ where each R$^{10}$ is independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where each R$^{10}$ is joined to form together with the nitrogen atom a heterocyclic or substituted heterocyclic ring.

"Alkenyl" refers to a monovalent alkenyl group having from 2 to 6 carbon atoms and more preferably 2 to 4 carbon atoms and having at least 1 and preferably from 1-2 sites of alkenyl unsaturation. The term "alkenyl" encompasses any and all combinations of cis and trans isomers arising from the presence of unsaturation. $C_2$ alkenyl groups are sometimes referred to herein as vinyl groups.

"Substituted alkenyl" refers to alkenyl groups having from 1 to 3 substituents, and preferably 1 to 2 substituents, selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not on a vinyl carbon atom. Substituted $C_2$ alkenyl groups are sometimes referred to herein as substituted vinyl groups.

"Alkynyl" refers to a monovalent alkynyl group having from 2 to 6 carbon atoms and more preferably 2 to 4 carbon atoms and having at least 1 and preferably only 1 site of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not on an unsaturated carbon atom.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocylic group provided that R' and R" are both not hydrogen. When R' is hydrogen and R" is alkyl or substituted alkyl, the substituted amino group is sometimes referred to herein as alkylamino. When R' and R" are alkyl or substituted alkyl, the substituted amino group is sometimes referred to herein as dialkylamino. When R' is hydrogen and R" is aryl or substituted aryl, the substituted amino group is sometimes referred to herein as arylamino. When R' and R" are aryl or substituted aryl, the substituted amino group is sometimes referred to herein as diarylamino.

"Acylamino" refers to the groups —NR$^{11}$C(O)alkyl, —NR$^{11}$C(O)substituted alkyl, —NR$^{11}$C(O)cycloalkyl, —NR$^{11}$C(O)substituted cycloalkyl, —NR$^{11}$C(O)alkenyl, —NR$^{11}$C(O)substituted alkenyl, —NR$^{11}$C(O)aryl, —NR$^{11}$C(O)substituted aryl, —NR$^{11}$C(O)heteroaryl, —NR$^{11}$C(O)substituted heteroaryl, —NR$^{11}$C(O)heterocyclic, and —NR$^{11}$C(O)substituted heterocyclic where R$^{11}$ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is to an aromatic ring atom. Preferred aryls include phenyl and naphthyl, e.g, 2-naphthyl.

"Substituted aryl" refers to aryl groups which are substituted with from 1 to 3 substituents, and preferably 1 to 2 substituents, selected from the group consisting of hydroxy, acyl, acylamino, alkyl, substituted alkyl, alkoxy, substituted alkoxy, alkenyl, substituted alkenyl, amino, substituted amino, aminoacyl, aryl, substituted aryl, aryloxy, substituted aryloxy, cycloalkoxy, substituted cycloalkoxy, carboxyl, carboxyl esters, cyano, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Arylthio" refers to the group aryl-S—.

"Carboxyl" refers to —COOH or pharmaceutically acceptable salts thereof.

"Carboxyl esters" refers to the groups —C(O)O-alkyl, —C(O)O— substituted alkyl, —C(O)Oaryl, and —C(O)O-substituted aryl wherein alkyl, substituted alkyl, aryl and substituted aryl are as defined herein.

"Cycloalkyl" refers to monovalent cyclic alkyl groups of from 3 to 10 carbon atoms having single or multiple condensed rings which condensed rings may or may not be cycloalkyl provided that the point of attachment is to a cycloalkyl ring atom. Examples of cycloalkyl groups include, by way of example, adamantyl, cyclopropyl, cyclobutyl, cyclopentyl, cyclooctyl and the like.

"Substituted cycloalkyl" refers to a cycloalkyl group, having from 1 to 5 substituents selected from the group consisting of oxo (═O), thioxo (═S), alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkenyl" refers to monovalent cyclic alkenyl groups of from 3 to 10 carbon atoms having single or multiple condensed rings which condensed rings may or may not be cycloalkyl provided that the point of attachment is to a cycloalkyl ring atom. Examples of cycloalkyl groups include, by way of example, adamantyl, cyclopropyl, cyclobutyl, cyclopentyl, cyclooctyl and the like.

"Substituted cycloalkyl" refers to a cycloalkyl group, having from 1 to 5 substituents selected from the group consisting of oxo (═O), thioxo (═S), alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to a monovalent aromatic group of from 1 to 15 carbon atoms, preferably from 1 to 10 carbon atoms, and 1 to 4 heteroatoms selected from the group consisting of oxygen, nitrogen, and —S— within the ring. The ring nitrogen and/or sulfur atoms are optionally oxidized to provide, for example, —SO—, and —SO$_2$— groups. Such heteroaryl groups can have a single ring (e.g., pyridyl or furyl) or multiple condensed rings (e.g., indolizinyl or benzothienyl) provided that the point of attachment is through a heteroaryl ring atom. Examples of suitable heteroaryls include pyridyl, pyrrolyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" refers to amonovalent saturated or unsaturated group having a single ring or multiple condensed rings, from 1 to 10 carbon atoms and from 1 to 4 hetero atoms selected from the group consisting of nitrogen, sulfur, and oxygen within the ring wherein, in fused ring systems, one or more the rings can be aryl or heteroaryl provided that the point of attachment is to a heterocyclic (non-aromatic) ring atom. The ring nitrogen and/or sulfur atoms are optionally oxidized to provide, for example, —SO—, and —SO$_2$— groups.

"Substituted heterocycle" or "substituted heterocyclic" refers to heterocyclic groups having from 1 to 5 substituents as defined above for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydro-benzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Optionally substituted vinyl group" as it relates to $R^4$ and $R^5$ refers to the group $>C=CR^{10}R^{11}$ where $R^{10}$ and $R^{11}$ are independently selected from the group consisting of hydrogen, halogen, alkyl, substituted alkyl, aryl, substituted aryl, heteroaryl, substituted heteroaryl, heterocyclic and substituted heterocyclic.

"Pharmaceutically acceptable salt" refers to pharmaceutically acceptable salts of a compound of any of Formulas I-V which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "platinum coordination compound" is used herein to denote any tumor cell growth inhibiting platinum coordination compound which provides platinum in the form of an ion.

The term "prodrug" refers to pharmaceutically acceptable, art recognized modifications to one or more functional groups which functional groups are metabolized in vivo to provide a compound of this invention or an active metabolite thereof. Such functional groups are well known in the art and preferably include acyl groups for hydroxyl and/or amino substitution, and the like.

The term "taxane compounds" indicates a class of compounds having the taxane ring system and related to or derived form extracts from certain species of yew (*Taxus*) trees.

The term "topisomerase" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has similar mechanism of action which involves the introduction of DNA strand breaks of the formation of free radicals.

The term "camptothecin compounds" is used to indicate compounds that are related to or derived from the parent camptothecin compound which is water-insoluble alkaloid derived from the Chinese tree *Camptothecin acuminate* and the Indian tree *Nothapodytes foetida*.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumor anthracycline derivatives" comprise antibiotics obtained from the fungus *Strep. peuticus* var. *caesius* and their derivatives, characterized by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is highly purified recombinant DNA-derived humanized monoclonal IgG1 kappa antibody that binds with high affinity and specificity to the extracellular domain of the HER2 receptor.

Many breast cancers have estrogen receptors and growth of these tumors can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, inhibiting its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promoters of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The terms "proteosome inhibitor" and "proteosomic agent" refer to agents, that inhibit enzymatic activity produced by the mammalian 26S proteosome. Compounds that exhibit this activity and which traverse the cell membrane generally act as cytotoxic agents. Proteosome inhibitors may be reversible, or irreversible, as described herein. These agents are generally useful in the treatment of cancer and inflammatory disorders.

The term "proliferative disorder" refers to one or more of a number of diseases or disorders characterized by abnormal cell proliferation, resulting in abnormal cell growth. Abnormal cell proliferation commonly occurs in neoplastic diseases (cancer), certain inflammatory conditions, including psoriasis, and certain neurodegenerative disorders, including Alzheimer's disease.

The terms "neoplastic disease" and "cancer" are used interchangeably and refer to any of a number of diseases in which abnormal cells divide without control. Cancer cells can invade nearby tissues and can spread through the bloodstream and lymphatic system to other parts of the body. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system. Within these major categories, various forms of cancer are generally named with reference to the tissue of origin, such as "renal cell carcinoma" (referring to tumors in or spreading from the renal tubules of the kidney) or "osteosarcoma" (referring to tumors in or spreading from the bone).

The term "tumor" refers to a mass of excess tissue that results from abnormal cell division. Tumors may be benign (not cancerous) or malignant (cancerous).

The terms "inflammatory condition," "inflammatory disorder" or inflammatory disease" are interchangeable herein and refer to any of a number of disorders characterized by one or more symptoms of an inflammatory response, which may be manifest by physiologic, cellular and/or molecular events, such as vasodilation, increased vascular permeability, fever, extravasation of plasma and consequent interstitial edema, chemotaxis of neutrophils, macrophages and lymphocytes, such as increased levels of certain cytokines (e.g., IL-1α, IL-1β, IL-6, generally IL-1 through IL17), tumor necrosis factor alpha (TNF-α); increased acute phase reactants, such as C-reactive protein; certain cellular adhesion molecules such as e-selectin (ELAM), integrins, ICAM-1, ICAM-3, BL-CAM, LFA-2, NCAM, PECAM and neopterin; leukotriene; thromboxzne; isoprostane; serum amyloid A protein, fibrinectin, fibrinogen; leptin; prostaglandin E2; serum procalcitonin; soluble TNF receptor 2; leukocytosis (increased white blood cell levels), hypoalbuminemia (impaired albumin production), activation of complement, stimulation of antibody production.

Inflammatory disorders include, but are not limited to diabetes, particularly inflammatory complications thereof, such as diabetes-associated nephropathy and retinopathy; protein wasting; muscle inflammation; cardiovascular diseases or disorders including atherosclerosis; neurodegenerative diseases, such as Alzheimer's disease; autoimmune encephalomyelitis; inflammatory components of disorders of infectious or non-specific origin, such as myocarditis, blepharitis, cardiomyopathy, acute endocarditis, percarditis; asthma; systemic inflammatory response syndrome (SIRS); adult respiratory distress syndrome (ARDS); rheumatoid arthritis; osteoarthritis; systemic lupus eryhematosis; airway hyperresponsiveness (AHR); brochial hyperreactivity; chronic obstructive pulmonary disease (COPD); congestive heart failure (CHF); metabolic syndrome, end stage renal disease (ESRD) and complications of renal dialysis; as well as a number of dermal (skin) inflammatory conditions, including psoriasis, eczema, rashes, pruritis, reactions to foreign toxins, such as insect bites, poison ivy, nettles and hives.

Anti-inflammatory agents are known in the art, and include, without limitation, non-steroidal anti-inflammatory agents (aspirin, salicylates, sasalate, dflunisal, sulfasalazine, olsalazine, acetaminophen, ibuprofen, naproxen, flurbiprofen, ketoprofen, fenoprofen, oxzprozin, feamates, oxicams, pyrazolidinediones, nabumetone, indomethacin, sulindac, etodolac, tolmetin, diclofenac, ketorolac, apazone), 5-lipoxygenase inhibitors (zileuton, piripost, docebenone, tenidap), gold salts, steroids (cortisol, cortisone, fludrocortisone, prednisone, prednisolone, 6α-methylprednisolone, triamcinolone, betamethasone, dexamethasone).

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Still further, some of the compounds defined herein include vinyl groups which can exist in cis, trans or a mixture of cis and trans forms. All combinations of these forms are within the scope of this invention.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

As to the synthesis of compounds of this invention, Scheme 1 below illustrates a general method for synthesis of lactacystin analogs wherein Y is >CR$^4$R$^5$, Y' is NR$^3$ and Y" is oxygen:

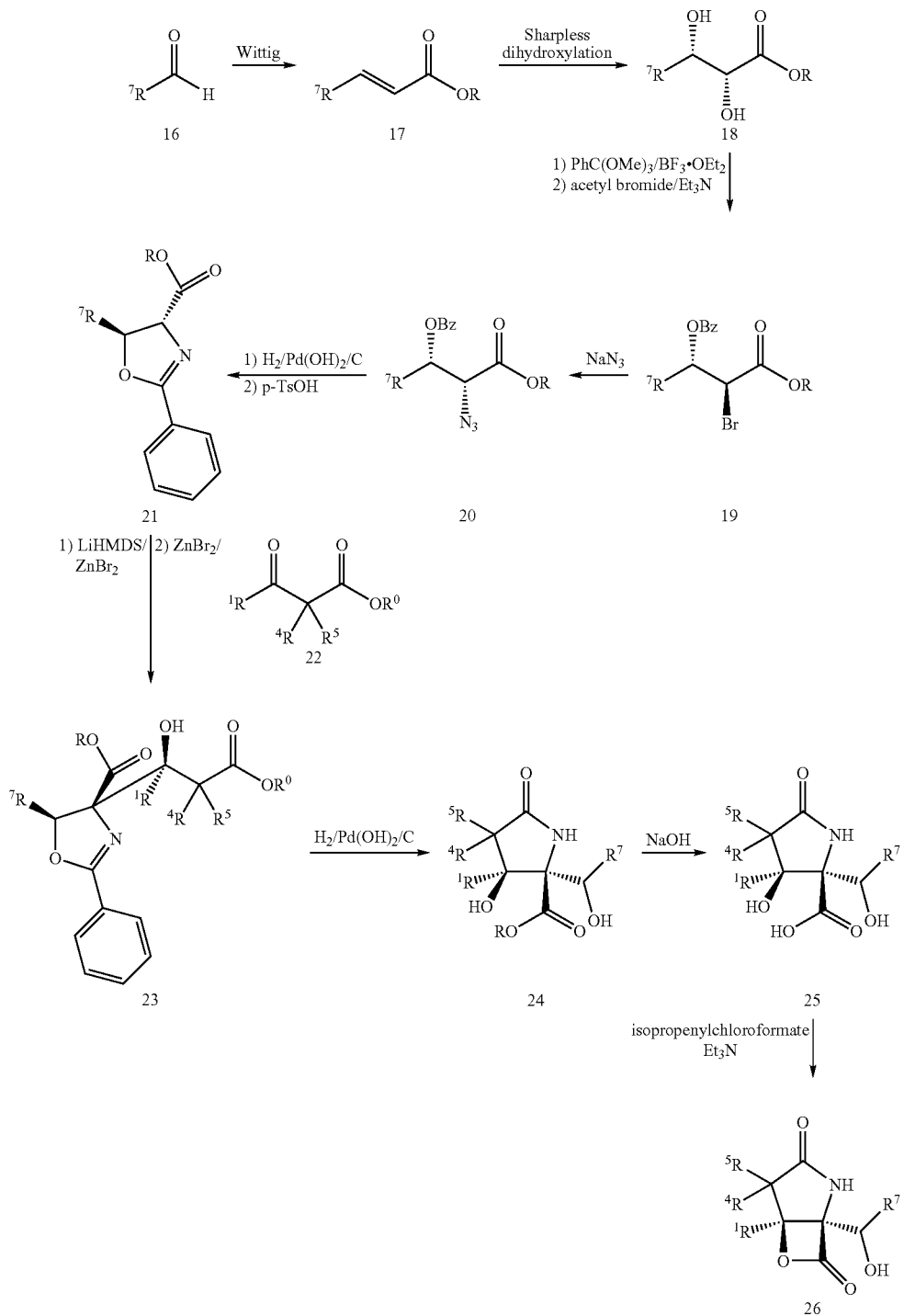

where R and R° are $C_1$-$C_3$ alkyl and $R^1$, $R^4$, $R^5$, and $R^7$ are as defined above.

In Scheme 1, a commercially available aldehyde, compound 16, is subject to a conventional Wittig Horner reaction to provide for the trans-3-alkyl acrylate, compound 17. This reaction is carried out as per the method described in the literature, for example, using dialkyl phosphonate in the presence of a strong base such as n-BuLi or preferably sodium hydride in an organic solvent, for example, anhydrous ethers such as diethyl ether, dibutyl ether, dioxane, preferably anhydrous tetrahydrofuran under inert atmosphere such as nitrogen or argon atmosphere at a reaction temperature from 0° C. to 80° C., preferably at a reaction temperature between about 5° C. and about 50° C. Upon reaction completion, the compound 17 is recovered by conventional methods including neutralization, evaporation, extraction, precipitation, chromatography, filtration, and the like, or, alternatively, is used in the next reaction without purification and/or isolation.

Conventional Sharpless dihydroxylation of the vinyl group of trans-3-alkyl acrylate, compound 17, provides for the corresponding alkyl 2,3-dihydroxylpropionate, compound 18. For example, the Sharpless dihydroxylation reaction is known in the art and permits the transformation of an olefin to a vicinal diol in a predictable, non-racemic fashion with the requisite disposition for further elaboration. For example, this reaction may be carried out by combining an olefin, a chiral ligand, an organic solvent, water, an osmium catalyst and an oxidant under suitable reaction conditions to form a diol in a stereoselective manner. The chiral ligand, osmium catalyst, and oxidant used in this reaction may be obtained commercially as a mixture. One skilled in the art will recognize that other chiral ligands may be used and the choice will depend upon the desired enantioselectivity. Examples of other suitable reaction conditions for carrying out the Sharpless reaction are described for example, in PCT patent application publication number WO 91/16322, and the article by Kolb et al., Catalytic Asymmetric Dihydroxylation, Chem. Rev. 94, p. 2483-2547 (1994). The disclosures of these documents are incorporated herein by reference in their entireties. Upon reaction completion, the compound 18 is recovered by conventional methods including neutralization, evaporation, extraction, precipitation, chromatography, filtration, and the like, or, alternatively, is used in the next reaction without purification and/or isolation.

Alkyl 2,3-dihydroxylpropionate, compound 18, is converted to the corresponding alkyl 2-bromo-3-benzoyloxypropionate, compound 19, first by reaction with trimethylortho benzoate in the presence of $BF_3.Et_2O$ complex which provides for a cyclic intermediate (not shown) which is ring opened by the addition of acetyl bromide in the presence of triethylamine ($Et_3N$) to provide for the 2-bromo-3-benzoyloxy substituents. Ring opening results in inversion of the stereochemistry of the bromo group relative to the precursor hydroxyl group.

Alkyl 2-bromo-3-benzoyloxypropionate, compound 19, is converted to the corresponding alkyl 2-azido-3-benzoyloxypropionate, compound 20, by displacement of the bromo group with sodium azide. As in the previous reaction, there occurs an inversion of the stereochemistry of the azido group relative to the precursor bromo group.

Conventional hydrogenation of the azido group with hydrogen over a $Pd(OH)_2$/carbon hydrogenation catalyst provides for the corresponding amine (not shown) which then cyclizes in the presence of a suitable acid catalyst such as p-toluene sulfonic acid (pTSA) to provide for 2-phenyl oxazoline, compound 21.

Alkylation at the 4-position of the oxazoline ring coupled with inversion of the carboxylate stereochemistry proceeds under specificed conditions. Specifically, a slight excess of a suitable base such as lithium bis(trimethylsilyl)amide (LiHMDS) and a zinc salt such as $ZnBr_2$ is employed to generate a zinc enolate which then proceeds under nucleophilic conditions in the presence of an excess of a β-ketocarboxylic acid ester, compound 22, and $ZnBr_2$ to provide for compound 23.

Hydrogenation of compound 23 in the presence of a $Pd(OH)_2$/carbon hydrogenation catalyst results in oxazoline ring opening whereupon the deprotected amine functionality spontaneously cyclizes via nucleophilic attack on the carboxylate functionality [—C(O)OR°] and elimination of the alcohol, R°OH to provide for compound 24.

Conventional hydrolysis of the ester of 24 provides for compound 25 which undergoes lactone formation thereby forming compound 26 via contact of compound 25 with a slight excess of isopropenyl chloroformate in the presence of a suitable base, e.g., triethylamine. Upon reaction completion, the compound 26 is recovered by conventional methods including neutralization, evaporation, extraction, precipitation, chromatography, filtration, and the like.

As noted in Scheme 1 above, compound 20 is hydrogenated to an amino acid ester of the formula:

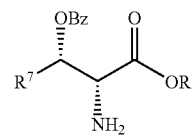

20a where R and $R^7$ are as defined above.

The precursors to some of these amino acid esters are commercially available as serine derivatives, e.g.,

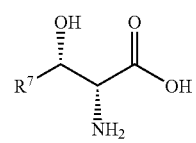

27

Where available, these amino acids can be transformed to the corresponding ester by conventional methods such as that illustrated in Scheme 2 below:

SCHEME 2

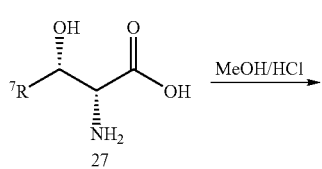

27

-continued

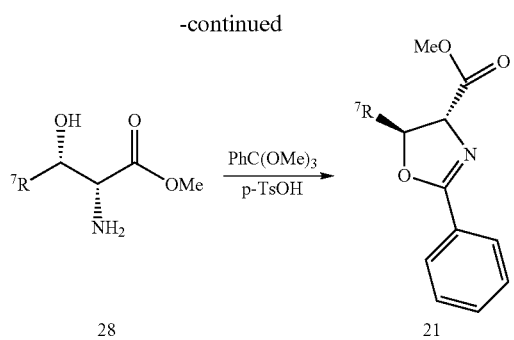

Specifically, amino acid, compound 27, is esterified in an acidic methanol solution to provide for the methyl ester, compound 28. In turn, compound 28 is cyclized in the manner described above to provide for compound 21.

Many of the β-ketocarboxylic acid esters encompassed by compound 22 are commercially available. Scheme 3 below illustrates a synthetic protocol for the synthesis of those β-ketocarboxylic acid esters which are not.

pound 29 with an excess of LiHMDS and subsequently having this enolate undergo nucleophilic coupling in the manner described above to form intermediate 32. As before, when $R^5$ is hydrogen, this coupling reaction proceeds once to introduce the $R^4$ substituent. When $R^5$ is other than hydrogen, this coupling reaction is conducted twice (as shown in Scheme 3). Intermediate 32 is then coupled with Weinreb amide, compound 30, in the presence of LiHMDS to form β-keto carboxyl ester, compound 22.

Finally, Scheme 4 illustrates the synthesis of Weinreb amide, compound 30, from the corresponding carboxylic acids, compound 33.

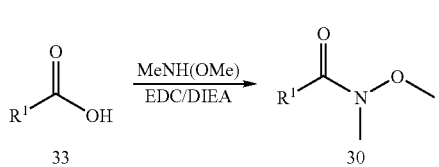

SCHEME 3

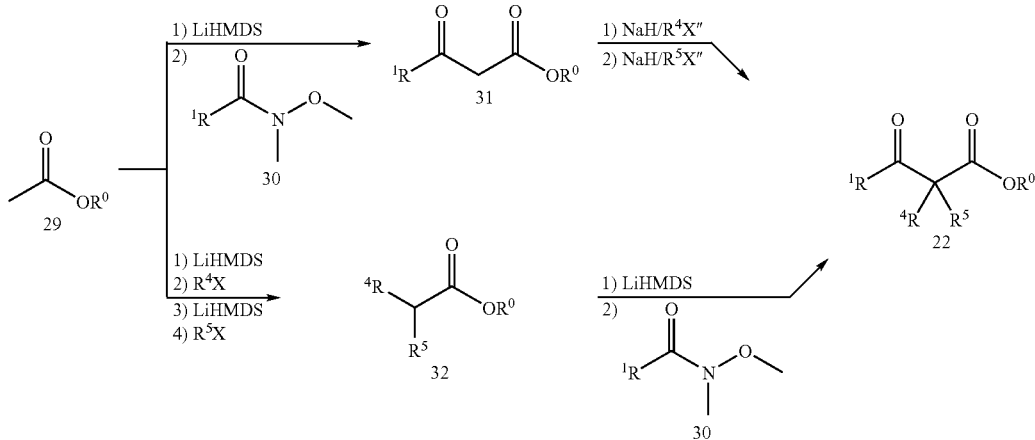

where $X^{11}$ is chloro, bromo, iodo, sulfonate or other suitable leaving group such as a mesyl or tosyl group and $R^o$, $R^1$, $R^4$ and $R^5$ are as defined above.

Specifically, in Scheme 3, acetic acid ester, compound 29, is coupled with Weinreb amide, compound 30, in the presence of lithium bis(trimethylsilyl)amide (LiHMDS) to form β-keto acetic acid ester, compound 31. Modification of compound 31 to introduce $R^4$ and optionally $R^5$ groups proceeds via conventional coupling conditions. Specifically, the reaction is conducted in the presence of a suitable base such as sodium hydride to generate an enolate (not shown) which then undergoes nucleophilic coupling to provide for compound 22. If $R^5$ is hydrogen, this coupling reaction proceeds once to introduce the $R^4$ substituent. When $R^5$ is other than hydrogen, this coupling reaction is conducted twice (as shown in Scheme 3).

Alternatively, as shown in Scheme 3, acetic acid ester, compound 29, can be first derivatized to introduce the $R^4$ and optionally the $R^5$ substituents by formation of the corresponding enolate (not shown) from contacting com- Such conversions are well known in the art and the starting carboxylic acids, 33, are typically commercially available but otherwise can be prepared by art recognized techniques.

In compound 26, conversion of the carbonyl groups to thiocarbonyl groups proceeds via conventional procedures such as contact with $P_2S_5$.

Additionally, Schreiber, et al., International Patent Application No. WO 96/32105 provides further synthetic details for the synthesis of compounds of this invention. This reference is incorporated herein by reference in its entirety.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I-V above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The compounds may be formulated for parenteral administration by injection. e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions. Alternatively, the active ingredient may be in powder form for constitution with a suitable vehicle, e.g., sterile pyrogen-free water, before use.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Lactose | 5 |
| Active Ingredient | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
| --- | --- |
| Active Ingredient | 250.0 mg |
| Isotonic saline | 1000 mL |

FORMULATION EXAMPLE 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another formulation that may be employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

Proteasomic inhibitory compositions of the present invention are useful in the treatment and/or amelioration of cell proliferative diseases or conditions, such as various forms of cancer and inflammatory conditions, as described herein. Test compounds may be selected as therapeutic or drug candidates using one or more of preclinical in vitro or in vivo assays known in the art. This section provides guidance for selecting proteosomic inhibitory compounds, using exemplary preclinical assays, but is not intended to limit the scope of such assays or of the invention.

Inhibition of proteasome activity has a wide range of biological effects, including, characterized by overall decrease of cellular protein degradation and heat-shock responses. These activities result in a number of biologically useful effects, including, without limitation, cytotoxicity, anti-tumor effects, and anti-inflammatory activities.

Recent development in the understanding of the regulation of the transcription factor, nuclear factor-κB (NF-κB), and its key role in pathogenesis of many inflammatory and neoplastic disorders provide a rationale for the use of proteasome inhibitors in the treatment of a wide range of inflammatory diseases such as asthma, arthritis, autoimmune encephalomyelitis, as well as in cerebral ischemia (stroke).

Although most cells are protected against toxic stimuli from short-term exposure to proteasome inhibitors through induction of heat shock response, long-term exposure is toxic to nearly all cells and causes cell death by apoptosis. Several studies have demonstrated that proliferating cell lines are more sensitive to proteasome inhibitors than non-proliferating cells to undergo apoptosis, probably due to several factors including cell cycle arrest caused by the inhibition of the proteasome, stabilization of the tumor suppressor protein p53, prevention of activation of the potent apoptosis inhibitor NF-κB, inactivation of growth factors such as interleukin-4 (IL-4) and IL-6. Bortezormib has recently been approved to treat multiple myeloma, providing clinical validation of the proteasome as a target for cancer therapies.

Selection of Proteosomic Inhibitory Compositions

Compounds of the present invention are selected for proteosomic inhibitory activity according to methods known in the art. By way of example, but not limitation, one convenient assay is the fluorogenic proteosome activity kit, which is commercially available from Chemicon International, Inc. (Temecula, Calif.). This assay, the details of which are provided in Example 14, herein, measures the ability of a test compound to inhibit proteolytic activity of a purified 20S proteasome on a fluorogenic peptide substrate, Suc-LLVY-AMC. Activity of test compounds is compared to that exhibited by known inhibitors lactacyctin and clasto-lactacystin β-lactone (Chemicon International, Inc., Temecula, Calif.). A test compound is considered to have requisite proteasome inhibitory activity, if it exhibits an $IC_{50}$ that is less than about 10 µM, more preferably less than about 2.5 µM, and even more preferably less than about 1 µM.

Further in vitro assays may be used to assess a compound's ability to inhibit cell proliferation, particularly in cancer cell lines, which are considered to be predictive of anti-tumor or anti-neoplastic activity. By way of example, the National Cancer Institute of the National Institutes of Health maintains a bank of cancer cell lines, including, for example, cell cultures derived from various leukemias, non-small cell carcinoma, small cell carcinoma, breast, colon, ovarian, renal, and melanoma. Methods for testing compounds for growth inhibitory activity are known in the art, and are described in greater detail in Example 15 herein. A test compound is considered to have requisite anti-proliferative activity, if it inhibits cell proliferation by 50% (growth inhibitory concentration-50; $GI_{50}$) that is less than about 100 µM, more preferably less than about 50 µM, and even more preferably less than about 25 µM, and still preferably less than about 10 µM.

Test compounds can be further tested for in vivo activity for the particular indication, in standard models known in the art and/or described herein (Example 16). Such assays may also provide additional information on target in vivo dosages.

For anti-neoplastic activity, an exemplary tumor model is the mouse M21 Melanoma Model. The M21 melanoma model is prepared by subcutaneous injection of tumor cells into nude mice, according to methods known in the art. Positive control anti-tumor activity can be assessed using one or more standard anti-neoplastic agents. Initial test dosages from about 10 to about 500 mg/kg, preferably 50-250 mg/kg, are used to determine efficacy in this assay.

Also known in the art are a number of standard human xenograft tumor models, particularly mouse models of xenografts of human colon, pancreas prostate or ovarian tumors. (e.g., Pink, M., et al. Proc. Am. Assoc. Cancer Res. 2002, 43:158, incorporated herein by reference).

Anti-inflammatory activity can be assessed using one or more anti-inflammatory activity models known in the art. Two such models, the mouse arachidonic acid assay and the oxazolone sensitization assay, measure inflammatory response to noxious chemicals applied to mouse skin, as described in Example 16 herein. A third exemplary assay, also described in Example 16, the carrageenan-induced paw edema assay, provides further information on anti-inflammatory activity (Gabor, M., Mouse Ear Inflammation Models and their Pharmacological Applications, 2000; incorporated herein by reference), and may be predictive therapeutic activity in a number of inflammatory conditions.

Dosages and Ranges of Compounds

The amount of the composition administered for therapy will depend on a number of factors, including but not limited to the desired final concentration of the compound, the pharmacokinetic and pharmacodynamic properties of the compound, the size of the patient, physiological profile of the patient, and the like. The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

Determination of dosages is well within the empiric knowledge of persons skilled in the art; nonetheless, it can be appreciated that estimates of final dosages can be made by approximating the concentration of compound necessary to achieve a desired proteasomic inhibitory, anti-proliferative, anti-cancer or anti-inflammatory activity, such as the activities described above. Further refinement of this dose estimate can be made on the basis of activity in one or more preclinical models, such as the animal models exemplified in Example 16 herein. Extrapolation to a specified mammalian dosage range, or more particularly a human dosage range is well within the skill of the practitioner.

Typically, the amount of a single administration of a composition of the present invention can be about 0.1 to about 1,000 mg per kg body weight, or from about 0.1 to about 10,000 mg per kg or about 0.5 to about 1,000 mg per day. Any of these doses can be further subdivided into separate administrations, and multiple dosages can be given to any individual patient.

In some embodiments, compositions are administered in one dosing of a single formulation and in other embodiments, compositions are administered in multiple dosing of a single formulation within a specified time period. In some embodiments, the time period is between about 3 hours to about 6 hours. In other embodiments, the time period is between about 6 hours and 12 hours. In additional embodiments, the time period is between about 12 hours and 24 hours. In yet further embodiments, the time period is between about 24 hours and 48 hours. The administration of separate formulations can be simultaneous or staged throughout a specified time period, such that all ingredients are administered within the specified time period.

Administration of Compounds

Therapeutic compounds of the invention can be administered using one or more of a number of standard therapeutic modalities, including, without limitation, oral ingestion; various parenteral forms of administration, including, without limitation, intravenous (i.v.), intramuscular (i.m.), subcutaneous administration (s.c.), intraarterial administration (i.a.), intrathecal administration, intraperitoneal administration; sublingual administration, rectal administration, nasal insufflation (pulmonary absorption); topical administration to the mucous membranes, skin, or eye. The particular mode of administration will be determined, in part, by the physicochemical properties of the therapeutic composition, and also by the location of the desired therapeutic target in the body of the subject to be treated. Appropriate formulations for each of these modes will be well within the skill of the practitioner; further guidance for making such preparations is provided in the formulation section, above.

Intravenous administration is commonly used to deliver chemotherapeutic agents to cancer patients. This method has the advantage of allowing for precision and accuracy in delivering a desired concentration of drug to the blood. Infusion may be carried out over relatively long periods of time, to minimize irritation to the blood vessels and point of injection. Typically, dosages for anti-neoplastic agents are calculated as a function of body surface area (BSA) as $mg/m^2$, as opposed to body mass (mg/kg), and are measured against the maximum tolerated dose (MTD). Methods for determining BSA and for converting conventional dosages (mg/kg) to $mg/m^2$ are known in the art.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| bm = | broad multiplet; |
| br s = | broad singlet; |
| Calcd = | calculated; |
| cm = | centimeter; |
| d = | doublet; |
| dd = | doublet of doublets; |
| DCM = | dichloromethane; |
| DME = | dimethoxyethane; |
| DMF = | dimethylformamide; |
| (DHQ)$_2$PHAL = | (dihydoquinone)$_2$ 1,4-phthalazinediyl diether |
| DMSO = | methylsulfoxide; |
| EDTA = | ethylene diamine tetracetic acid; |
| eq. = | equivalents; |
| EtOAc = | ethyl acetate; |
| FTIR = | Fourier transfer infrared spectrum; |
| g = | gram; |
| HOAc = | acetic acid; |
| HPLC = | high performance liquid chromatography; |
| kg = | kilogram; |
| LiHMDS = | lithium bis(trimethylsilyl)amide; |
| LRSM = | low resolution mass spectrum; |
| m = | multiplet; |
| M = | molar; |
| MeOH = | methanol; |
| mg = | milligram; |
| MHz = | megahertz; |
| min = | minute; |
| mL = | milliliter; |
| mm = | millimeter; |
| mM - | millimolar; |
| mmol = | millimol; |
| MS = | mass spectrometry; |
| N = | normal; |
| NMR = | nuclear magnetic resonance; |
| ppm = | parts per million; |
| psi = | pounds per square inch; |
| q = | quartet; |
| RT = | room temperature; |
| s = | singlet; |
| t = | triplet; |
| TEA = | triethylamine; |
| TCA = | trichloroacetic acid; |
| TFA = | trifluoroacetic acid; |
| THF = | tetrahydrofuran; |
| TLC = | thin layer chromatography; |
| pTSA = | para-toluenesulfonic acid; |
| UV = | ultraviolet; |
| μg = | microgram; |
| μL = | microliter; |
| μm = | micron; |
| μM = | microMolar; |
| w/v = | weight to volume; and |
| v/v = | volume to volume |

All the chemicals (starting materials, reagents and solvents) were obtained from commercial suppliers and used without further purification.

Flash column chromatography was performed with silica (60-120 mesh) and a suitable solvent system such as EtOAc/hexane. Analytical reverse phase HPLC was done using a Waters HPLC system equipped with a UV detector and a Xterra MS C18 column (5 μm, 4.6×50 mm) using acetonitrile (with 0.1% TFA)/water (with 0.1% TFA) as the mobile phase.

$^1$H NMR spectra were recorded using a 300 MHz Varian spectrometer and the proton chemical shifts are expressed in ppm relative to internal standards (tetramethylsilane or solvent peak) and coupling constants (J) are expressed in hertz. Mass spectra were carried out using a Thermo-Finnigan LCQ-Advantage mass spectrometer.

Example 1

Synthesis of Compound 17 ($^7$R=isopropyl, R=methyl)

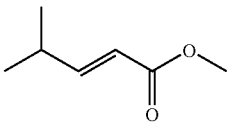

In a 500 mL round bottom flask fitted with a stirring bar, an addition funnel and a calcium chloride guard tube, methyl bromoacetate (18.6 mL, 0.196 mol) was taken in dry benzene (300 mL). The mixture was cooled to 0° C. and added with triphenylphosphine (51.4 g, 0.096 mol) in portions over a period of half an hour. The reaction mixture was warmed to room temperature and stirred for 24 hrs. The white solid obtained was filtered, washed with benzene and dried over vacuum to yield 75.5 g of Wittig salt. This salt was suspended in a mixture of dichloromethane/MeOH (125 mL/300 mL), cooled to 0° C., added with NaOH (8 g, 0.2 mol) in 30 mL of water and tetrabutylammonium bromide (0.58 g, 1 mol %), slowly warmed to RT, and stirred for 1 hr. The layers were separated. The aqueous layer was extracted with dichloromethane (3×50 mL). The combined organic layer was dried over sodium sulfate and concentrated to afford Ph$_3$P═CHCOOMe as a white solid (58 g, 88%).

To a cooled solution (0° C.) of Ph$_3$P═CHCOOMe (50 g, 0.15 mol) in dry dichloromethane (150 mL), isobutraldehyde (15 mL, 0.165 mol) was added dropwise at 0° C. over a period of 10 minutes. The reaction mixture was slowly warmed to RT and stirred for 24 hrs. The excess solvent was removed under reduced pressure and the residue was treated with petroleum ether (250 mL). The triphenylphosphine oxide precipitate was filtered off. This process was repeated two to three times to remove the maximum triphenylphonsphine oxide. The filtrate was concentrated and purified by silica gel column chromatography using EtOAc/petroleum ether to yield 17 (7.22 g, 34%): R$_f$ 0.5, EtOAc/petroleum ether (3:7, v/v).

Example 2

Synthesis of Compound 18 ($^7$R=isopropyl, R=methyl)

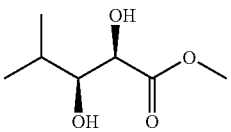

An admixture was prepared by mixing K$_2$OsO$_4$.2H$_2$O (0.136 g, 0.37 mmol), (DHQ)$_2$PHAL (0.306 g, 0.39 mmol), N-methyl morpholine-N-oxide (6.9 g, 58 mmol) in t-BuOH/H2O (90 mL, 1:1, v/v) at RT. To this mixture neat olefin 17 (5 g, 39 mmol) was added slowly over a period of 7 hrs and the mixture was stirred for 24 hrs. The reaction mixture was diluted with EtOAc (15 mL) and quenched with sodium sulfate (7.9 g, 63 mmol) in water (25 mL). The reaction mixture was stirred for 3-4 hrs. The layers were separated and the aqueous layer was extracted with EtOAc (3×15 mL).

The combined organic layer was dried over sodium sulfate, concentrated under reduced pressure and purified by silica gel column chromatography using EtOAc/petroleum ether to afford a mixture of diastereomers as a white low melting solid. The crude product was recrystalized using petroleum ether to get yield the desired diastereomer 18 (3 g, 48%) as a low melting white solid: Rf 0.4, EtOAc.

Example 3

Synthesis of Compound 19 (⁷R=isopropyl, R=methyl)

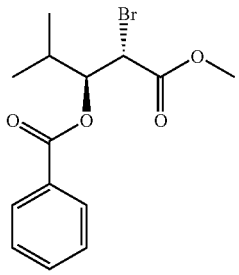

To a stirred solution of 18 (2.92 g, 18 mmol) in dry dichloromethane (30 mL), trimethyl orthobenzoate (4.33 mL, 25.2 mmol) and BF$_3$.diethyl ether (0.11 mL, 0.9 mmol) were added sequentially at RT and stirred for 2 hrs. More trimethly orthobenzoate (1.86 mL, 0.0108 mol) and BF$_3$.diethyl ether (0.11 mL, 0.8 mmol) were added and stirring was continued for 1 hr. The solvent was removed under reduced pressure and the residue was dried over high vacuum. The resulting yellow oil was dissolved in dry dichloromethane (30 mL), cool to 0° C., added with freshly distilled acetyl bromide (1.4 mL, 18.9 mmol), and stirred for 2 hrs. More acetyl bromide (0.07 mL, 0.9 mmol) was added at 0° C. and stirring was continued at RT for 12 hrs. The reaction mixture was treated with saturated aqueous NaHCO$_3$ solution (60 mL) and stirred vigorously for 10 minutes. The mixture was extracted with EtOAc (3×15 mL). The combined organic layer was dried over sodium sulfate and concentrated under reduced pressure to yield crude 19 (6 g, 100%) as a yellow pale oil, which was taken into next step without further purification.: R$_f$ 0.7, EtOAc/petroleum ether (1.5:8.5, v/v).

Example 4

Synthesis of Compound 20 (⁷R=isopropyl, R=methyl)

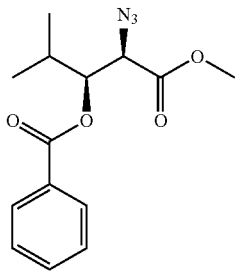

Sodium azide (2.56 g, 39.4 mol) was taken in dry DMSO (58 mL) and stirred for 12 hrs under nitrogen atmosphere. To this heterogeneous mixture 19 (6.0 g, 18.2 mmol) in dry DMSO (2 mL) was added and the reaction was stirred for 6 hrs at ambient temperature. To the reaction mixture, water (60 mL) and diethyl ether (30 mL) was added. The layers were separated, and the aqueous layer was extracted with ether (3×20 mL). The combined organic layer was dried over sodium sulfate and concentrated under reduced pressure. The resulting crude product 20 (4.61 g, 86%) was taken into the next step without further purification: R$_f$ 0.5, EtOAc/petroleum ether (9:1, v/v).

Example 5

Synthesis of Compound 21 (⁷R=isopropyl, R=methyl)

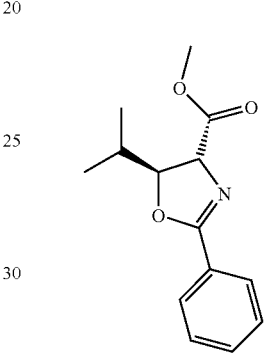

To a cooled (0-5° C.) solution of 20 (4.61 g, 0.0158 mol) in MeOH (30 ml) was added 4.0 M HCl in dioxane (9.2 ml) and Pd(OH)$_2$/C (0.368 g). The mixture was slowly warmed to RT and hydrogenated under hydrogen pressure for 5 hrs. More Pd(OH)$_2$/C (0.108 g) was added and hydrogenation was continued overnight. The reaction mixture was diluted with MeOH (25 ml), filtered through a Celite bed, and washed with MeOH (3×10 ml). The combined filtrate was concentrated, treated with water (915 ml) and solid Na$_2$CO$_3$ (till pH 9-10), and extracted with EtOAc (3×20 ml). The combined organic layer was dried over sodium sulfate and concentrated to give a thick brown oil, which was further purified by silica gel column chromatography using EtOAc/petroleum ether (3:7, v/v) to yield a brown gum (1.57 g, 37%): R$_f$ 0.3, EtOAc/petroleum ether (1:1, v/v).

To the above crude intermediate (1.57 g, 0.0059 mol) in dry toluene (15 mL), p-toluene sulfonic acid (0.11 g, 0.00059 mol) was added. The reaction was refluxed using Dean-Stark apparatus for 4 hrs. The reaction mixture was cooled to RT, diluted with 10 mL of EtOAc, washed with 10% aqueous NaHCO$_3$ solution (2×10 mL) and brine (15 mL), dried over sodium sulfate, and concentrated under reduced pressure. The crude product was further purified by silica gel column chromatography using EtOAc/petroleum ether (1:9, v/v) to yield 21 as a pale yellow oil (0.98 g, 68%): R$_f$ 0.2, EtOAc/petroleum ether (3:7, v/v); $^1$H NMR (300 MHz, CDCl$_3$) δ 8.01-7.95 (m, 2H), 7.52-7.45 (m, 1H), 7.45-7.37 (m, 2H), 4.66 (t, J=6.7 Hz, 1H), 4.56 (d, J=6.9 Hz, 1H), 3.80 (s, 3H), 2.04-1.88 (m, 1H), 1.03 (d, J=6.9 Hz, 3H), 1.00 (d, J=6.6 Hz, 3H); LRMS, [M+H] 248, calcd for C$_{14}$H$_{17}$NO$_3$ 247.

Example 6

Synthesis of Compound 21 ($^7$R=cyclohexyl, R=methyl)

Following similar procedures for Example 1-5, compound 21 ($^7$R=cyclohexyl, R=methyl) was synthesized: $^1$H NMR (300 MHz, CDCl$_3$), δ 8.01-7.98 (m, 2H), 7.55-7.40 (m, 3H), 4.75-4.61 (m, 2H), 3.80 (s, 3H), 1.90-52 (m, 6H), 1.40-1.02 (m, 5H); LRMS, [M+H] 288, calcd for C$_{17}$H$_{21}$NO$_3$ 287.

Example 7

Synthesis of Compound 22 ($^7$R=cyclopenthyl, R=methyl)

Following similar procedures for Example 1-5, compound 22 ($^7$R=cyclopenthyl, R=methyl) was synthesized: $^1$H NMR (300 MHz, CDCl$_3$): δ 8.02-7.98 (m, 2H), 7.55-7.38 (m, 3H), 4.80 (t or dd, J=10.0 Hz), 4.58 (d, J=10.0 Hz), 1.95-1.22 (m, 8H). LRMS, [M+H] 274, calcd for C$_{16}$H$_{19}$NO$_3$, 273.

Example 8

Compound 23 (R$^4$=H, R$^5$=methyl, $^7$R=isopropyl, R=methyl, R$^o$=ethyl)

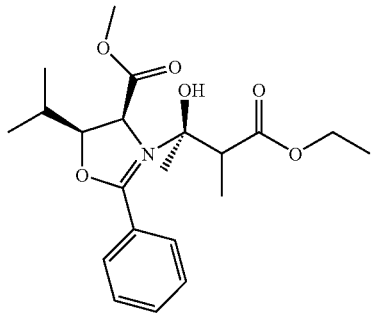

Oxazoline 21 (124 mg, 0.50 mmol, 1 eq.) was placed in a reaction vessel, flushed with dry nitrogen, dissolved in anhydrous, oxygen-free THF (2 mL, freshly distilled from Na-benzophenone), and cooled to −78° C. (dry ice-acetone). LiHMDS (0.55 mL, 1.0 M/hexane, 0.55 mmol, 1.1 eq.) was added dropwise (slow enough to minimize temperature increase) under nitrogen. The resulting bright orange solution was stirred under nitrogen at −78° C. for 30 min. Anhydrous ZnBr$_2$ (135 mg, 0.60 mmol, 1.2 eq.) was quickly weighed into a reaction vessel, dried under high vacuum for 30 min, flushed with nitrogen, dissolved in anhydrous, oxygen-free THF (1.0 mL), and added to the reaction at −78° C. dropwise (slow enough to minimize temperature increase). The resulting bright yellow solution was stirred under nitrogen at −78° C. for another 30 min. In the mean time, another potion of anhydrous ZnBr$_2$ (135 mg, 0.60 mmol, 1.2 eq.) was quickly weighed into a reaction vessel, dried under high vacuum for 30 min, flushed with dry nitrogen, dissolved in anhydrous, oxygen-free THF (1.0 mL), added with ethyl 2-methylacetoacetate 22 (R$^1$=methyl, R$^4$=H, R$^5$=methyl, R$^o$=ethyl, 87 μL, 0.60 mmol, 1.2 eq), stirred under nitrogen at RT for 30 min, and added to the above zinc enolate solution at −78° C. (slowly to minimize temperature increase). The reaction was stirred at −78° C. for 4 hrs and stood in a −78° C. freezer for overnight (12 hrs) under nitrogen. HOAc (150 μL, 2.5 mmol, 5 eq.)/THF (1.0 mL) was added dropwise (slowly to minimize temperature increase) under nitrogen at −78° C. The reaction was stirred at −78° C. for 10 min before warming up to RT. EtOAc (50 mL) was added and the solution was washed with saturated NH$_4$Cl (50 mL×2) and saturated NaHCO$_3$ (50 mL×1), dried over Na$_2$SO$_4$, concentrated under vacuum at RT. The oily crude product was quickly purified on a silica gel column with 0%, 10%, and 20% EtOAc/hexane to yield the desired product 23 (73 mg, 37%) as a thick, colorless oil: R$_f$ 0.80, 40% EtOAc/hexane (v/v); $^1$H NMR (300 MHz, CDCl$_3$) δ 7.97-7.91 (m, 2H), 7.52-7.45 (m, 1H), 7.44-7.37 (m, 2H), 4.88 (d, J=3.3 Hz, 1H), 4.36-4.18 (m, 2H), 4.01 (br s, 1H), 3.76 (s, 3H), 2.74 (q, J=6.9 Hz, 1H), 2.22-2.11 (m, 1H), 1.42 (s, 3H), 1.30 (t, J=6.9 Hz, 3H), 1.22 (d, J=6.9 Hz, 3H), 1.15 (d, J=7.2 Hz, 3H), 0.80 (d, J=6.3 Hz, 3H); LRMS, [M+H] 392, calcd for C$_{21}$H$_{29}$NO$_6$ 391. The product has limited stability and should be subjected to the subsequent reaction as soon as possible.

A roughly 1:1 mixture of cis:trans starting oxazoline 21 was also recovered as a colorless oil (66 mg, 53%), which can be recycled in the reaction.

Example 9

Synthesis of Compound 24 (R$^1$=methyl, R$^4$=H, R$^5$=methyl, $^7$R=isopropyl, R=methyl)

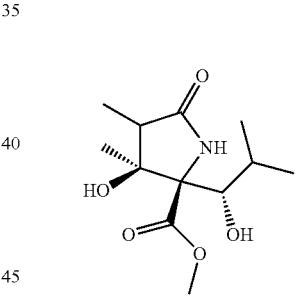

Compound 23 (115 mg, 0.29 mmol) was dissolved in MeOH (9 mL) in a 20 mL vial. HOAc (1 mL) and Pd(OH)$_2$/C (230 mg, 0.16 mmol, 0.5 eq.) were added. The vial was placed in a steel pressure vessel, flushed with hydrogen (5 times), pressurized with hydrogen to 55 psi, and stirred at RT for 72 hrs. The pressure was carefully released. The catalyst was filtered off with a celite pad, washed with MeOH (2 mL×4). The solutions were combined and concentrated under vacuum at RT to dryness. The residue was re-dissolved in toluene and concentrated under vacuum at RT. This process was repeated for two more times to remove traces of HOAc. The crude product was purified on silica gel with 20%, 40%, and 80% EtOAc/hexane to yield the desired lactam 24 as a colorless oil (26 mg, 35%): R$_f$ 0.50, EtOAc; $^1$H NMR (300 MHz, CDCl$_3$) δ 6.16 (br s, 1H), 4.25 (d, J=3.3 Hz, 1H), 3.77 (s, 3H), 2.32 (q, J=7.2 Hz, 1H), 1.98-1.86 (m, 1H), 1.35 (s, 3H), 1.17 (d, J=7.2 Hz, 3H), 1.03 (d, J=6.9 Hz, 3H), 0.92 (d, J=6.6 Hz, 3H); LRMS, [M+H] 260, calcd for C$_{12}$H$_{21}$NO$_5$ 259.

Example 10

Compound 25 (R$^1$=methyl, R$^4$=H, R$^5$=methyl, $^7$R=isopropyl)

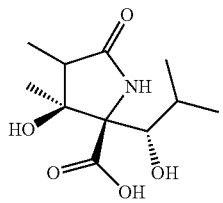

Methyl ester 24 (8.0 mg, 0.031 mmol, 1 eq.) was suspended in water (1 mL) by brief sonication at RT and cooled to 0° C. Pre-cooled (0° C.) 0.2 N NaOH/H$_2$O solution was added dropwise with stirring. The reaction was vigorously stirred from 0° C. to RT for 12 hr, quenched by dropwise addition of 1 N HCl/H$_2$O (0.22 mL, final pH 3-4), concentrated at rt to dryness. The white reside was re-suspended in toluene (5 mL) and concentrated to dryness. The residue was suspended in THF (2 mL) by brief sonication. Anhydrous Na$_2$SO$_4$ (0.5 g) was added. The mixture was vigorously stirred for 5 min, filtered through a Na$_2$SO$_4$ plug, washed with more THF (2 mL×4). The THF solutions were combined, concentrated, and dried under high vacuum for overnight to afford the crude dihydroxy carboxylic acid 25: R$_f$ 0.20, HOAc:MeOH:DCM (1:9:30, v/v/v).

Example 11

Synthesis of Compound 26 (R$^1$=methyl, R$^4$=H, R$^5$=methyl, $^7$R=isopropyl)

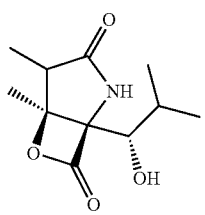

The above dihydroxy carboxylic acid 25 (0.031 mmol, 1 eq.) was dissolved in anhydrous THF (3 mL), added with TEA (13 µL, 0.094 mmol, 3 eq.) and isopropenyl chloroformate (5 µL, 0.046 mmol, 1.5 eq.), and stirred at RT for 3 hrs. The reaction was quenched with minimum water (2 µL, 0.11 mmol, 4 eq.), stirred for 5 min, diluted with EtOAc (5 mL), filtered through an anhydrous Na$_2$SO$_4$ plug, and washed with more EtOAc (2 mL×4). The EtOAc solutions were combined and concentrated to dryness. The residue was quickly chromatographed on silica gel with 0%, 30%, and 60% EtOAc/hexane to afford lactone 26 (2 mg) as a white solid: R$_f$ 0.50, EtOAc; $^1$H NMR (300 MHz, pyridine-d$_5$) δ 10.42 (br s, 1H), 7.20 (br m, 1H), 4.05 (br m, 1H), 3.00 (q, J=7.5 Hz, 1H), 2.30 (m, 1H), 1.93 (s, 3H), 1.43 (d, J=7.8 Hz, 3H), 1.37 (d, J=6.9 Hz, 3H), 1.31 (d, J=6.3 Hz, 3H); LRMS, [M+H—CO$_2$] 184, calcd for C$_{11}$H$_{17}$NO$_4$ 227; FTIR 3410 cm$^{-1}$, 2950 cm$^{-1}$, 1828 cm$^{-1}$, 1705 cm$^{-1}$, 1550 cm$^{-1}$, 671 cm$^{-1}$.

Example 12

Alternative Synthesis of Compound 21 ($^7$R=isopropyl, R=methyl)

In a 2-neck round bottom flask (500 mL), fitted with a CaCl$_2$ guard tube, anhydrous MeOH (150 mL) was added and dry HCl was bubbled slowly at 0° C. About 50-60 g of dry HCl was collected. (2R,3S)-3-Hydroxyleucine (27, $^7$R=isopropyl, 5.0 g, 34 mmol) was added to the methanolic HCl solution in small portions. The reaction mixture was refluxed at 65° C. for 24 h. The reaction flask was cooled to RT and methanol was removed under vacuum to yield a viscous liquid. The viscous liquid was dried under high vacuum for 6 h to furnish the hydrochloride of compound 28 ($^7$R=isopropyl, R=methyl) (6.60 g, 98% yield) as a hygroscopic semi-solid material.

To a solution of 28 (6.60 g, 0.033 mol) in DME (100 mL) was added trimethylorthobenzoate (18.25 g, 0.10 mol, 3 eq) and the reaction mixture was refluxed at 100° C. for 8 h. The reaction progress was monitored by TLC and it showed presence of some baseline material. The reaction mixture was refluxed for additional 6 h and then cooled to RT. DME was removed under vaccum and water (100 mL) was added to the viscous residue. Aqueous layer was extracted with ether (2×100 mL). Ether layer was dried (anhyd. Na$_2$SO$_4$) and concentrated under vacuum to furnish a viscous oil. Flash column chromatography on SiO$_2$ afforded the pure oxazoline 21 (6.32 g, 77% yield) as a colorless viscous oil: R$_f$ 0.50 (EtOAc/hexane, 3:7, two runs); H$^1$ NMR δ CDCl$_3$: 1.0-1.10 (two d, 6H, two CH$_3$), 2.0 (m, 1H, —CH—), 3.80 (s, 3H, —COOMe), 4.60 (d, 1H, —CH—), 4.70 (dd, 1H, —CH—), 7.40-7.60 (m, 3H, aromatic H), 8.0 (d, 2H, aromatic H).

Example 13

Synthesis of Compound 22 ($^4$R=methyl, $^5$R=H)

To a solution of β-keto ester (31, 10 g, 1.0 eq) in anhydrous DMF, under argon atmosphere (100 mL), anhydrous Li$_2$CO$_3$ (2.50 eq) was added in one portion. The reaction mixture was stirred at RT for about 10 minutes. Methyl iodide (2.50 eq) was added dropwise and the resulting suspension was stirred at 50° C. The reaction progress was monitored by TLC and HPLC. The starting material disappeared in about 17-24 h. After completion, the reaction mixture was quenched carefully by pouring into water (200 mL) containing con. HCl (20 mL). The aqueous layer was extracted with ether (2×150 ml) and the organic layer was washed with water (2×100 mL), dried (anhydrous Na$_2$SO$_4$) and concentrated under vacuum to furnish the crude product as viscous oil. The pure product, 2-methyl-α-ketoester was obtained as a colorless oil by flash chromatography on SiO$_2$ using hexane-ether mixture as the eluent.

Compund 22 ($^1$R=phenyl, $^4$R=methyl, $^5$R=H, $^0$R=ethyl), Ethyl-2-methyl-benzoylacetate (10.30 g, 97% yield, reference: KE-II-147): R$_f$ 0.70 (ether/hexane, 2:8, v/v); H$^1$NMR (CDCl$_3$) δ 1.20 (t, 3H, COOEt), 1.50 (d, 3H, CH$_3$), 4.15 (q, 2H, COOEt), 7.40-7.65 (m, 3H, aromatic H), 8.0 (d, 2H, aromatic H).

Compund 22 ($^1$R=ethyl, $^4$R=methyl, $^5$R=H, $^0$R=ethyl), Ethyl-2-methyl-benzoylacetate Ethyl-2-methyl-propionylacetate (5.50 g, 50% yield): R$_f$ 0.60 (hex-ether 80:20); H$^1$NMR δ CDCl$_3$, 1.10 (t, 3H, CH$_3$), 1.30 (t, 3H, CH$_3$), 1.35 (d, 3H, CH$_3$), 2.50 (q, 2H, CH$_2$), 3.50 (q, 1H, CH), 4.20 (q, 2H, COOEt).

Compund 22 ($^1$R=n-propyl, $^4$R=methyl, $^5$R=H, $^0$R=ethyl), Ethyl-2-methyl-butyroylacetate (6.70 g, 62% yield): $R_f$ 0.60 (hex-ether 80:20); H$^1$NMR δ CDCl$_3$, 0.90 (t, 3H, CH3), 1.25 (t, 3H, CH$_3$), 1.30 (d, 3H, CH$_3$), 1.60 (q, 2H, CH$_2$), 2.50 m, 2H, CH$_2$), 3.50 (q, 1H, CH), 4.20 (q, 2H, COOEt).

Compund 22 ($^1$R=cyclopropyl, $^4$R=methyl, $^5$R=H, $^0$R=methyl), Methyl-3-cyclopropyl-2-methyl-3-oxo-propionate (5.70 g, 52% yield): $R_f$ 0.55 (hex-ether 90:10); H$^1$NMR δ CDCl$_3$, 0.90-0.95 (m, 2H, CH$_2$), 1.05-1.10 (m, 2H, CH$_2$), 1.40 (d, 3H, CH$_3$), 2.0-2.10 (m, 1H, CH), 3.65-3.70 (q, 1H, CH), 3.75 (s, 3H, COOMe).

Example 14

Proteasome Inhibitory Assay

Commercial 20S proteasome assay kits, including all reagents described below, are available from a number of commercial vendors, such as Chemicon International, Inc. (Temecula, Calif.). Assays are carried out according to kit instructions. Purified 20S proteasome (0.5 μg/μL) is pre-incubated with test inhibitory compound (dissolved in <5% v/v DMSO as co-solvent) in a buffer (25 mM HEPES, 0.5 mM EDTA, 0.05% Nonidet P-40 (NP-40) detergent, 0.001% sodium laurel sulfate (SDS), pH 7.5) at room temperature in a 96-well fluorometer plate. A fluorogenic substrate for chymotrypsin-like activity (Suc-LLVY-AMC) is added, according to manufacturer's directions, and the plate is incubated at 37° C. for 1 hr. The fluorescence signal ($λ_{ex}$: 380 nm; ($λ_{em}$: 440 nm) is read in a fluorometer (Perkin-Elmer Wallac Victor; Perkin Elmer, Wellesley, Mass.). Activity of test compounds is compared to that exhibited by known inhibitors lactacyctin and clasto-lactacystin β-lactone (Chemicon International, Inc., Temecula, Calif.).

A test compound is considered to have requisite proteasome inhibitory activity, if it exhibits an IC$_{50}$ that is less than about 10 μM, more preferably less than about 2.5 μM, and even more preferably less than about 1 μM.

Example 15

Anti-proliferation Assay

Anti-proliferative activity: Compounds exhibiting proteasome inhibition activity in the above enzymatic assay will also be evaluated for anti-proliferative activity against the National Cancer Institute (NCI) cancer cell line panel, which comprises multiple cell lines representing leukemias, non-small cell carcinoma, small cell carcinoma, breast, colon, ovarian, renal, and melanoma. The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO$_2$, 95% air and 100% relative humidity for 24 h prior to addition of test agent(s).

After 24 h, two plates of each cell lines are fixed in situ with TCA, to represent a measurement of the cell population for each cell line at the time of inhibitor addition. Proteasome inhibitors are solubilized in DMSO at 400-fold the desired final maximum test concentration and stored frozen prior to use. At the time of inhibitor addition, an aliquot of frozen concentrate is thawed and diluted to twice the desired final maximum test concentration with complete medium containing 50 μg/mL gentamicin. Additional four-fold, 10-fold or ½ log serial dilutions are made to provide a total of five inhibitor concentrations plus control. Aliquots of 100 μL of these different inhibitor dilutions are added to the appropriate microtiter wells already containing 100 μL of medium, resulting in the required final inhibitor concentrations.

Following addition of test compound, the plates are incubated for an additional 48 h at 37° C., 5% CO2, 95% air and 100% relative humidity. For adherent cells, the assay is terminated by the addition of trichloroacetic acid (TCA). Cells are fixed in situ by the gentle addition of 50 μL of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μL) at 0.4% (w/v) in 1% acetic acid is added to each well, and the plates are incubated for 10 minutes at room temperature. After staining, unbound dye is removed by washing five times with 1% acetic acid and the plates are air dried. Bound stain is subsequently solubilized with 10 mM trizma base, and the absorbance is read on a plate reader at 515 μm. For suspension cells, the procedure is the same except that the assay is terminated by fixing settled cells at the bottom of the wells by gently adding 50 μL of 80% TCA (final concentration, 16% TCA).

A test compound is considered to have requisite anti-proliferative activity, if it inhibits cell proliferation by 50% (growth inhibitory concentration-50; GI$_{50}$) that is less than about 100 μM, more preferably less than about 50 μM, and even more preferably less than about 25 μM, and still preferably less than about 10 μM.

Example 16

In Vivo Assays

1. Anti-cancer Activity

M21 Melanoma Model. The M21 melanoma model is prepared by subcutaneous injection of tumor cells into nude mice. When tumors reach a size of about 50-250 cm$^3$, the mice receive four doses of placebo or test compound by intravenous injection every other day. Tumor volume is measured until the tumor quadruples in size. Positive control anti-tumor activity can be assessed using one or more standard anti-proliferative agents, according to methods known in the art. P-values can be determined using Tukey's W procedure with normalized tumor volumes 13 days post treatment, and for tumor quadrupling times. Initial test dosages from about 10 to about 500 mg/kg, preferably 50-250 mg/kg, are used to determine efficacy in this assay.

Human Xenograft Models (Pink, M., et al. *Proc. Am. Assoc. Cancer Res.* 2002, 43: 158). Further studies are carried out, as indicated in, standard human xenograft models, particularly mouse models of xenografts of human colon, pancreas prostate or ovarian tumors.

2. Anti-inflammatory Activity

Mouse arachidonic acid assay. Albino male CD-1 mice, 7-9 weeks old are used in this test. A 20% (w/v) arachidonic acid solution in acetone is prepared. Twenty microliters of the arachidonic acid solution is applied to the dorsal left ear of the mouse. Immediately thereafter, test compounds (20 microliters in 70% ethanol/30% propylene glycol) are applied to the left ear. The untreated right ears served as control. Mice are sacrificed by carbon dioxide inhalation, one hour after treatment. The left and right ears are removed and 7 mm punch biopsies taken from each. The punch biopsies are weighed, and the differences calculated.

Oxazolone-induced Inflammation Model. CD-1 mice are induced by applying 3% oxazolone (Sigma) (30 mg/ml prepared in corn oil:acetone) to the shaved abdomen. Five days later, the mice are challenged with 2% oxazolone (20 mg/mL) in acetone on the left ear (right ear was untreated control). One hour after challenge, test compounds are applied to the left ear in 70% ethanol/30% propylene glycol. Animals are sacrificed 24 hours later and 7 mm ear punches are removed. The ear punches are placed on a balance scale, and the difference between the untreated and treated ears is determined. Percent inhibition is calculated by comparing the means of each group to the vehicle group. (Hydrocortisone serves as a positive control in this test.)

Carrageenan-induced Paw Edema. In vivo evaluation of anti-inflammatory activity can be determined by well characterized assays such as reduction of carrageenan-induced paw edema in rats (Gabor, M., Mouse Ear Inflammation Models and their Pharmacological Applications, 2000). Carrageenan-induced paw edema is a model of inflammation, which causes time-dependent edema formation following carrageenan administration into the intraplantar surface of a rat paw.

What is claimed is:

1. A compound of formula I:

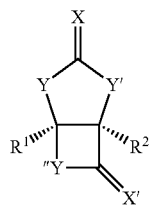

wherein:
- $R^1$ is selected from the group consisting of alkyl, substituted alkyl, cycloalkyl, substituted cycloalkyl, cycloalkenyl, substituted cycloalkenyl, alkenyl, substituted alkenyl, alkynyl, substituted alkynyl, aryl and substituted aryl;
- $R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;
- X and X' are independently selected from the group consisting of oxygen, sulfur and $NR^3$ where $R^3$ is independently selected from the group consisting of hydrogen, hydroxyl, amino, alkyl, substituted alkyl, cycloalkyl, substituted cycloalkyl, aryl, substituted aryl, alkoxy, aryloxy, alkylamino, arylamino, and acylamino;
- Y is selected from the group consisting of —O—, —N($R^3$)—, —S— and —C($R^4$)($R^5$)—;
- Y' is —N($R^3$)—; and
- Y'' is —O—;

wherein:
- $R^3$ is as defined above and $R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further $R^4$ and $R^5$ together with the carbon atom pendent thereto form an optionally substituted vinyl group; or
- prodrugs, isomers and pharmaceutically acceptable salts thereof.

2. A compound of formula II:

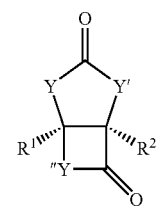

wherein:
- $R^1$ is selected from the group consisting of alkyl, substituted alkyl, cycloalkyl, substituted cycloalkyl, cycloalkenyl, substituted cycloalkenyl, alkenyl, substituted alkenyl, alkynyl, substituted alkynyl, aryl and substituted aryl;
- $R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;
- Y is selected from the group consisting of —O—, —N($R^3$)—, —S— and —C($R^4$)($R^5$);
- Y' is —N($R^3$)—; and
- Y'' is —O—;

wherein:
- $R^3$ is independently selected from the group consisting of hydrogen, hydroxyl, amino, alkyl, substituted alkyl, cycloalkyl, substituted cycloalkyl, aryl, substituted aryl, alkoxy, aryloxy, alkylamino, arylamino, and acylamino;
- $R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, substituted aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further $R^4$ and $R^5$ together with the carbon atom pendent thereto form an optionally substituted vinyl group; or
- prodrugs, isomers and pharmaceutically acceptable salts thereof.

3. A compound of formula III:

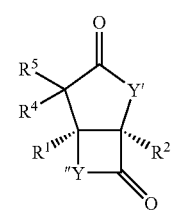

wherein:
- $R^1$ is selected from the group consisting of alkyl, substituted alkyl, cycloalkyl, substituted cycloalkyl, cycloalkenyl, substituted cycloalkenyl, alkenyl, substituted alkenyl, alkynyl, substituted alkynyl, aryl and substituted aryl;

$R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;

$R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, substituted aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further $R^4$ and $R^5$ together with the carbon atom pendent thereto form an optionally substituted vinyl group;

Y' is —N($R^3$)—; and
Y" is —O—;

wherein:
$R^3$ is independently selected from the group consisting of hydrogen, hydroxyl, amino, alkyl, substituted alkyl, cycloalkyl, substituted cycloalkyl, aryl, substituted aryl, alkoxy, aryloxy, alkylamino, arylamino, and acylamino; and $R^4$ and $R^5$ are as defined above; or prodrugs, isomers and pharmaceutically acceptable salts thereof.

4. A compound of formula IV:

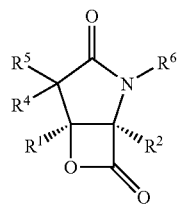

IV wherein:
$R^1$ is selected from the group consisting of alkyl, substituted alkyl, cycloalkyl, substituted cycloalkyl, cycloalkenyl, substituted cycloalkenyl, alkenyl, substituted alkenyl, alkynyl, substituted alkynyl, aryl and substituted aryl;

$R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;

$R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, substituted aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further $R^4$ and $R^5$ together with the carbon atom pendent thereto form an optionally substituted vinyl group;

$R^6$ is selected from the group consisting of hydrogen, hydroxyl, amino, substituted amino, acylamino, alkyl, substituted alkyl, cycloalkyl, substituted cycloalkyl, aryl, substituted aryl, alkoxy, substituted alkoxy, aryloxy, and substituted aryloxy, or prodrugs, isomers and pharmaceutically acceptable salts thereof.

5. A compound of formula V:

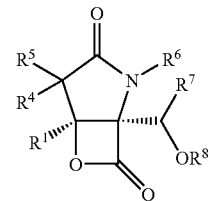

V wherein:
$R^1$ is selected from the group consisting of alkyl, substituted alkyl, cycloalkyl, substituted cycloalkyl, cycloalkenyl, substituted cycloalkenyl, alkenyl, substituted alkenyl, alkynyl, substituted alkynyl, aryl and substituted aryl;

$R^2$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;

$R^4$ and $R^5$ are independently selected from the group consisting of hydrogen, halo, alkyl, substituted alkyl, alkoxy, substituted alkoxy, cycloalkyl, substituted cycloalkyl, alkenyl, substituted alkenyl, alkynyl, substituted alkynyl, aryl, substituted aryl, aryloxy, substituted aryloxy, acyloxy, amino, substituted amino, acylamino, alkylthio, arylthio, and acylthio or $R^4$ and $R^5$ together with the carbon atom pendent thereto form an optionally substituted cycloalkyl group or further $R^4$ and $R^5$ together with the carbon atom pendent thereto form an optionally substituted vinyl group;

$R^6$ is selected from the group consisting of hydrogen, hydroxyl, amino, substituted amino, acylamino, alkyl, substituted alkyl, cycloalkyl, substituted cycloalkyl, aryl, substituted aryl, alkoxy, substituted alkoxy, aryloxy, and substituted aryloxy;

$R^7$ is selected from the group consisting of hydrogen, alkyl, substituted alkyl, cycloalkyl, substituted cycloalkyl, alkenyl, substituted alkenyl, alkynyl, substituted alkynyl, aryl and substituted aryl;

$R^8$ is selected from the group consisting of hydrogen, alkyl, substituted alkyl, cycloalkyl, substituted cycloalkyl, aryl and substituted aryl; or prodrugs, isomers and pharmaceutically acceptable salts thereof.

6. A compound according to claim 1, wherein $R^1$ is selected from the group consisting of methyl, trifluoromethyl, methoxymethyl, ethyl, 2-methoxyethyl, n-propyl, iso-propyl, iso-butyl, n-butyl, cyclopropyl, cyclobutyl, cyctopentyl, cyclohexyl, cyclohexenyl, vinyl, ethynyl, allyl, benzyl, and phenyl.

7. A compound according to claim 1, wherein $R^2$ is selected from the group consisting of 1-hydroxyl-2-methylpropane-1-yl, and 1-hydroxyl-1-cyclohexylmethane-1-yl.

8. A compound according to claim 1, wherein $R^3$ hydrogen or methoxy.

9. A compound according to claim 1, wherein Y is >$CR^4R^5$.

10. The compound of claim 9, wherein $R^4$ is selected from the group consisting of $(C_1-C_6)$alkyl, halo$(C_1-C_6)$alkyl, halogen, $(C_1-C_6)$alkoxy, $(C_1-C_6)$alkylthio, phenoxy, $(C_1-C_6)$alkylamino, and $(C_1-C_6)$acylamino.

11. The compound of claim 9, wherein $R^5$ is selected from the group consisting of hydrogen, fluoro, and chloro.

12. The compound of claim 9, wherein $R^4$ and $R^5$ are joined to form a group selected from a cycloalkyl group, a vinyl group and a substituted vinyl group.

13. A compound according to claim 5, wherein $R^7$ is selected from the group consisting of $(C_3-C_6)$alkyl, cycloalkyl, and cycloalkenyl.

14. A compound according to claim 5, wherein $R^8$ is hydrogen.

15. A pharmaceutical composition, comprising an effective amount of a compound according to claim 1, and a pharmaceutically inert carrier.

16. A pharmaceutical composition, comprising an effective amount of a compound according to claim 1, an effective amount of at least one anti-neoplastic agent, and a pharmaceutically inert carrier.

17. A pharmaceutical composition, comprising an effective amount of a compound according to claim 1, an effective amount of at least one anti-inflammatory agent, and a pharmaceutically inert carrier.

* * * * *